United States Patent
Black et al.

(10) Patent No.: US 9,671,180 B2
(45) Date of Patent: Jun. 6, 2017

(54) PROCESS ANALYTIC DEVICE WITH IMPROVED THERMAL STABILITY

(71) Applicant: Rosemount Analytical Inc., Houston, TX (US)

(72) Inventors: Steven S. Black, Houston, TX (US); Edward J. Bailey, Cypress, TX (US); Leighton M. Fields, Rosharon, TX (US)

(73) Assignee: Rosemount Analytical, Inc, Houston, TX (US)

( * ) Notice: Subject to any disclaimer, the term of this patent is extended or adjusted under 35 U.S.C. 154(b) by 329 days.

(21) Appl. No.: 14/498,192

(22) Filed: Sep. 26, 2014

(65) Prior Publication Data

US 2015/0013430 A1 Jan. 15, 2015

Related U.S. Application Data

(63) Continuation-in-part of application No. 13/826,720, filed on Mar. 14, 2013, now Pat. No. 9,228,983.

(60) Provisional application No. 61/932,949, filed on Jan. 29, 2014.

(51) Int. Cl.
| | |
|---|---|
| *G01N 30/30* | (2006.01) |
| *G01N 30/66* | (2006.01) |
| *G01N 30/02* | (2006.01) |
| *G01N 30/72* | (2006.01) |
| *G01N 30/88* | (2006.01) |
| *F28F 9/007* | (2006.01) |
| *F28D 15/02* | (2006.01) |

(52) U.S. Cl.
CPC .............. *F28F 9/007* (2013.01); *F28D 15/02* (2013.01); *G01N 30/30* (2013.01); *G01N 30/66* (2013.01); *G01N 2030/8886* (2013.01)

(58) Field of Classification Search
CPC .. B01D 15/34; B01D 15/08; G01N 2030/025; G01N 30/02; G01N 2030/3046; G01N 30/7206; G01N 2030/3007; G01N 2030/3053; G01N 30/54
See application file for complete search history.

(56) References Cited

U.S. PATENT DOCUMENTS

| | | |
|---|---|---|
| 3,828,184 A | 8/1974 | Lupton |
| 4,096,908 A | 6/1978 | Lamy |
| 5,043,576 A | 8/1991 | Broadhurst et al. |
| 5,588,988 A | 12/1996 | Gerstel et al. |

(Continued)

FOREIGN PATENT DOCUMENTS

| | | |
|---|---|---|
| CN | 201314906 Y | 9/2009 |
| CN | 204666576 | 9/2015 |
| DE | 3047601 A | 7/1982 |

OTHER PUBLICATIONS

First Office Action from Chinese Application No. 201510046869.4, from May 5, 2016, 8 pages, including English translation.

(Continued)

*Primary Examiner* — David A Rogers
(74) *Attorney, Agent, or Firm* — Christopher R. Christenson; Kelly, Holt & Christenson, PLLC

(57) ABSTRACT

A process analytic device includes an input to receive a sample of interest and an analytic detector operably coupled to receive the sample of interest. An analytic output is provided relative to the sample of interest. A plurality of heat pipes is thermally coupled to the analytic detector.

17 Claims, 4 Drawing Sheets

(56) References Cited

U.S. PATENT DOCUMENTS

| | | |
|---|---|---|
| 5,686,656 A | 11/1997 | Amirav et al. |
| 5,756,878 A | 5/1998 | Muto et al. |
| 5,778,681 A | 7/1998 | Li et al. |
| 5,808,179 A | 9/1998 | Sittler et al. |
| 5,954,860 A | 9/1999 | Gordon |
| 6,014,864 A * | 1/2000 | Owen ............... F25D 29/001 165/96 |
| 6,054,683 A | 4/2000 | Bremer et al. |
| 6,113,722 A | 9/2000 | Hoffman et al. |
| 6,134,945 A | 10/2000 | Gerstel et al. |
| 6,461,515 B1 | 10/2002 | Safir et al. |
| 6,465,777 B1 | 10/2002 | Rache |
| 6,907,796 B2 | 6/2005 | Bremer et al. |
| 8,378,293 B1 | 2/2013 | Quimby et al. |
| 8,726,747 B2 | 5/2014 | Kennett et al. |
| 2005/0268693 A1 | 12/2005 | Hasselbrink et al. |
| 2007/0107675 A1 | 5/2007 | Kurano |
| 2011/0107816 A1 | 5/2011 | Barth |
| 2011/0108568 A1 | 5/2011 | Hogan |
| 2012/0141345 A1 | 6/2012 | Slaten |
| 2012/0149125 A1 | 6/2012 | Earley et al. |
| 2012/0285223 A1 | 11/2012 | Andrews et al. |
| 2013/0071867 A1 | 3/2013 | Fadgen |
| 2013/0078609 A1 | 3/2013 | Tverskoy |
| 2013/0256523 A1 | 10/2013 | Steiner et al. |
| 2014/0260532 A1 | 9/2014 | Bailey et al. |

OTHER PUBLICATIONS

First Chinese Office Action for Application No. 201310254759.8, dated Apr. 3, 2015, 15 pages.
Second Office Action from Chinese Application No. 201310254759.8, from Oct. 9, 2015, 7 pages.

* cited by examiner

PROCESS ANALYTIC DEVICE WITH IMPROVED THERMAL STABILITY

CROSS REFERENCE TO RELATED APPLICATIONS

The present application claims is based on and claims the benefit of Provisional Patent Application Ser. No. 61/932,949, filed on Jan. 29, 2014, the content of which is hereby incorporated by reference in its entirety; and the present application is a Continuation-in-part Application of U.S. patent application Ser. No. 13/826,720, filed on Mar. 14, 2013.

BACKGROUND

Analytical devices and instruments are used in a number of applications to quantitatively and/or qualitatively analyze a sample of interest. Analytical devices and instruments are often found in laboratories and are sometimes employed within processing operations. As used herein, an analytical device is any device, system or arrangement that is able to receive a sample of interest and provide an indication of some aspect of the sample of interest. Analytical devices include, without limitation, process gas analyzers, NO/NOx analyzers, hydrocarbon analyzers, continuous emission monitoring systems and process gas chromatographs.

Gas chromatographs (GC) rely on precise control of temperature of chromatographic columns, detectors, and support systems. One or more electrical heaters are used to heat a controlled oven, chamber or locally heated zone or substrate (hereinafter oven). Such heaters operate by cycling on/off in a closed loop control system with temperature feedback provided by one or more temperature sensors in or near the oven. Such state of the art oven temperature control systems provide adequate control of a temperature set point (typically +/−0.1° C. or less) for the oven when external ambient conditions are stable. However, it is common for process gas chromatographs to be installed without protection from the ambient environment. Such exposed process gas chromatographs may experience ambient temperature variations from −40° to +60° C. but are still expected to deliver consistent measurement performance across such wide ambient variations.

As the art of process analytic devices has progressed, there is increasing pressure to provide a more precise analytic output even when faced with significant ambient temperature fluctuations.

The discussion above is merely provided for general background information and is not intended to be used as an aid in determining the scope of the claimed subject matter. The claimed subject matter is not limited to implementations that solve any or all disadvantages noted in the background.

SUMMARY

A process analytic device includes an input to receive a sample of interest and an analytic detector operably coupled to receive the sample of interest. An analytic output is provided relative to the sample of interest. A plurality of heat pipes is thermally coupled to the analytic detector.

BRIEF DESCRIPTIONS OF THE DRAWINGS

DETAILED DESCRIPTION

Figure 1:
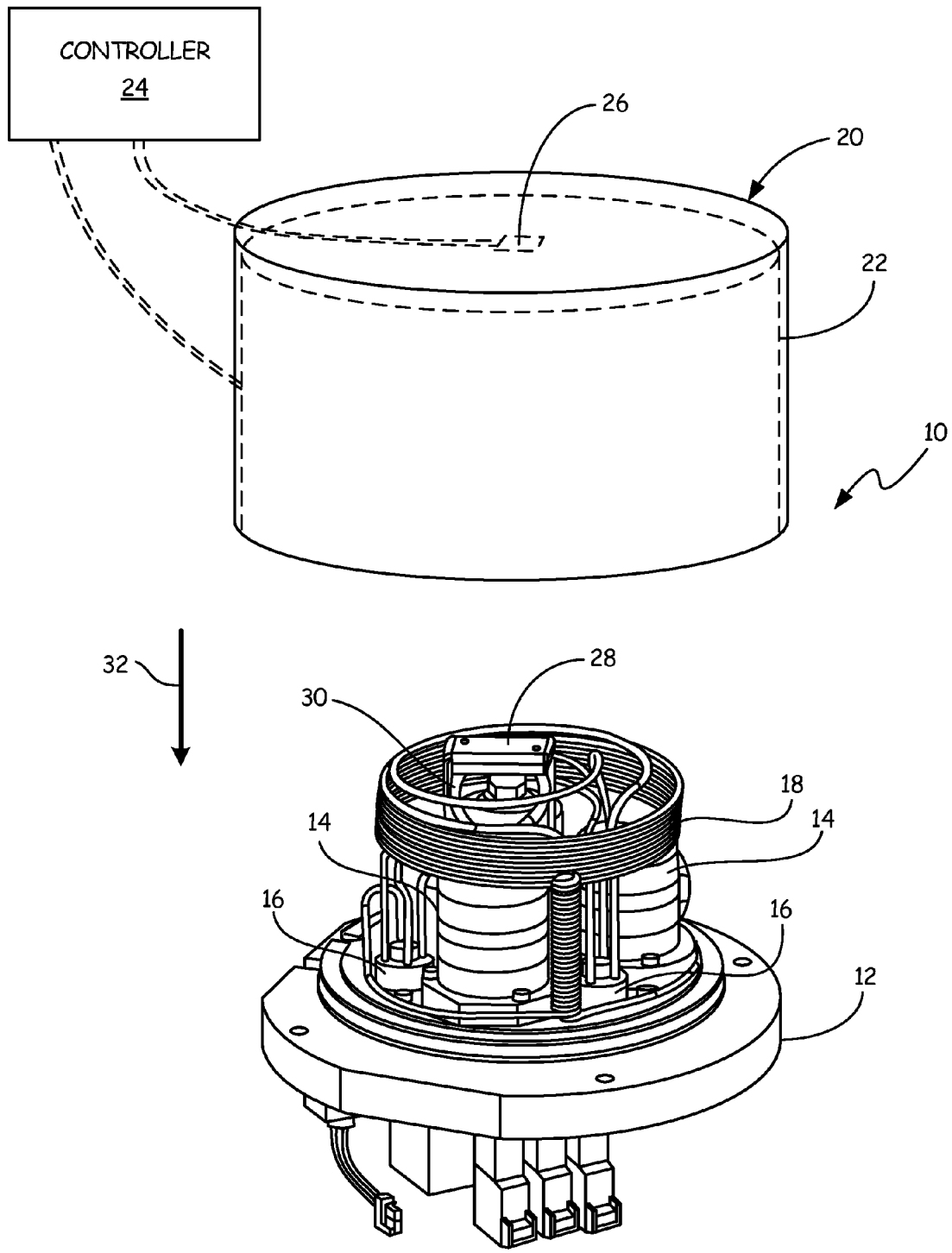
FIG. 1 is a diagrammatic view of a portion of a process gas chromatograph in accordance with an embodiment of the present invention.

Gas chromatograph generally employ an oven heater that controls an average oven temperature driven by one or more measurements from temperature sensors within the oven. Examples of such sensors include thermocouples, resistance temperature devices (RTD's) and thermistors. Commonly, a single temperature sensor is used. The single point measurement leads to performance compromises when heat losses from the oven occur as a result of external ambient temperature variations. Typically, as the oven loses heat, there is a lag time before the control sensor indicates to the control system that the average oven temperature has dropped and the control system responds by applying power to the heater(s). The result is that some oven surfaces or areas may have cooled below the control set point before heating is commanded by the control system and that other areas of the oven will achieve temperatures higher than the set point before the control system senses that enough heat has been added to the oven to achieve the set point. Thus, significant variations may occur in current chromatograph ovens as a result of ambient influences.

Thermal Conductivity Detectors (TCD's) are commonly used in gas chromatographs and function by measuring minute deviations in thermal conductivity of gases flowing through the detector. Such detectors are extremely sensitive to temperature variations; affecting measurement stability and precision. Generally, the location of a TCD in the chromatograph oven is not thermally symmetrical. As the oven control system and heater(s) respond to external influences, localized temperature variations occur within the oven as described above. These oven variations allow for thermal losses or gains through the TCD mount and/or TCD body to cause the localized temperature of the TCD body to vary as a result. Any such temperature deviation of the TCD itself results in measurement variation.

Embodiments of the present invention provide improved measurement performance of temperature sensitive detector (s) within a process analytic device by significantly improving thermal control relative to such detectors. Embodiments of the present invention generally employ one or more heat pipes to provide additional heating to the TCD body to counteract thermal losses and reduce the effect of thermal variations within the oven.

A heat pipe is generally formed as conduit constructed from of a relatively high thermal conductivity metal, such as copper. The conduit is generally evacuated and then provided with working fluid after which the conduit is sealed. Examples of working fluids include water, ethanol, and acetone. The working fluid is selected such that when it contacts the hot (evaporator) side of the heat pipe it absorbs heat and turns into vapor. The vapor then flows to the cold side where it releases thermal energy (cools) and condenses back to a liquid. The liquid then returns to the hot side via a capillary action or gravity and the process repeats.

Heat pipes are known and used for conducting heat from the hot (evaporator) to the cold (condenser) zone. Heat pipes are commonly used to remove waste heat (e.g. cooling a microprocessor), or to drive heat into a device from a remote heater. Heat pipe technology typically provides thermal conductivities 100-200 times that of copper. Heat pipe performance is such that significant heat flux can be moved across a small deviation in temperature between the evaporator and the condenser.

Embodiments of the present invention generally employ one or more heat pipes arranged in a manner that effectively couples the thermal conductivity detector body with the temperature-controlled oven. A heat pipe is generally a passive device that provides a high level of thermal coupling between its evaporator and its condenser. One embodiment of the present invention locates the heat pipe evaporator such that it extends into the precisely controlled oven with the heat pipe condenser located on or proximate the thermal conductivity detector itself. This arrangement provides a very stable heat source to add supplemental heating (or cooling) to the thermal conductivity detector based on the temperature of the heat pipe evaporator, without the need to have any additional control system to control heat pipe operation. The heat pipe evaporator is ideally located in the area of the oven determined to be most precisely thermally controlled and most immune to external thermal influences; typically near the temperature sensor of the thermal control system for the oven. Thus, the heat source for the heat pipe is exceptionally stable and provides more precise control than a modulated supplemental heater. This stable passive heat source pumps heat from the most stable area of the oven to the thermal conductivity detector body. This, in turn, helps compensate for heat demand variation induced by external influences. Sourcing the heat from the most isothermal area of the oven provides supplemental heating to the thermal conductivity detector body at a constant temperature providing less actual deviation in practice than the oven control provides for. This arrangement eliminates the need for a supplemental heater and controller and/or additional insulation or thermal conductivity detector isolations. This steady state source of supplemental heat minimizes variation of the thermal conductivity detector body and thus provides for improved measurement performance in a varying environment.

FIG. 1 is a diagrammatic perspective view of a portion of a process gas chromatograph 10. FIG. 1 illustrates a portion of an upper, thermally-controlled portion of process gas chromatograph 10. Specifically, chromatograph 10 includes base plate 12 which, in one embodiment, is formed of an amorphous thermoplastic polyetherimide (PEI) resin such as that sold under the trade designation Ultem, available from SABIC Innovative Plastics of the Netherlands. A plurality of multi-port flow valves 14 are mounted on base plate 12, along with a plurality of multi-port distribution fittings 16. Additionally, one or more suitable detectors for the process gas chromatograph, such as thermal conductivity detector 34 (shown in FIG. 2), are also mounted on or proximate base plate 12. One or more chromatographic separation columns are typically mounted proximate the various flow devices within an environmentally-sealed cover 20. A sample shut-off valve (not shown) which cuts off flow of sample gas during certain valve actuation configurations may be mounted within proximity of the other flow devices.

Within cover 20, one or more heaters 22 maintain precise thermal control of the entire assembly 10. For example, for process gas chromatography, the entire assembly 10 is typically maintained at approximately 80° C. plus or minus a fraction of a degree C. Heaters 22 are coupled to a controller 24 that may be a component of the process gas chromatograph 10 or separate. Controller 24 is also coupled to one or more temperature sensors 26 in order to determine the temperature within cover 20. Controller 24 selectively applies power to heaters 22 based on the measured temperature in order to provide precise thermal control within cover 20. This precise thermal control allows controller 24 to maintain the temperature of the sample of interest and the analytic detector at a specified temperature. However, as set forth above, it is possible for small thermal fluctuations to occur based on heat flow, time lag, and the control regime.

As shown in FIG. 1, a protective metal shield 28 is provided around heat pipe 30. When cover 20 is moved in the direction indicated by arrow 32 and mounted or otherwise affixed to process gas chromatograph 10, heaters 22 substantially encircle columns 18, valves, 14 and fittings 16. Additionally, temperature sensor 26, mounted to or within cover 20, is thermally coupled to metal shield 28. Shield 28, being metal, has a relatively high thermal conductivity and ensures that heat pipe 30 is in close thermal contact with temperature sensor 26.

Figure 2:
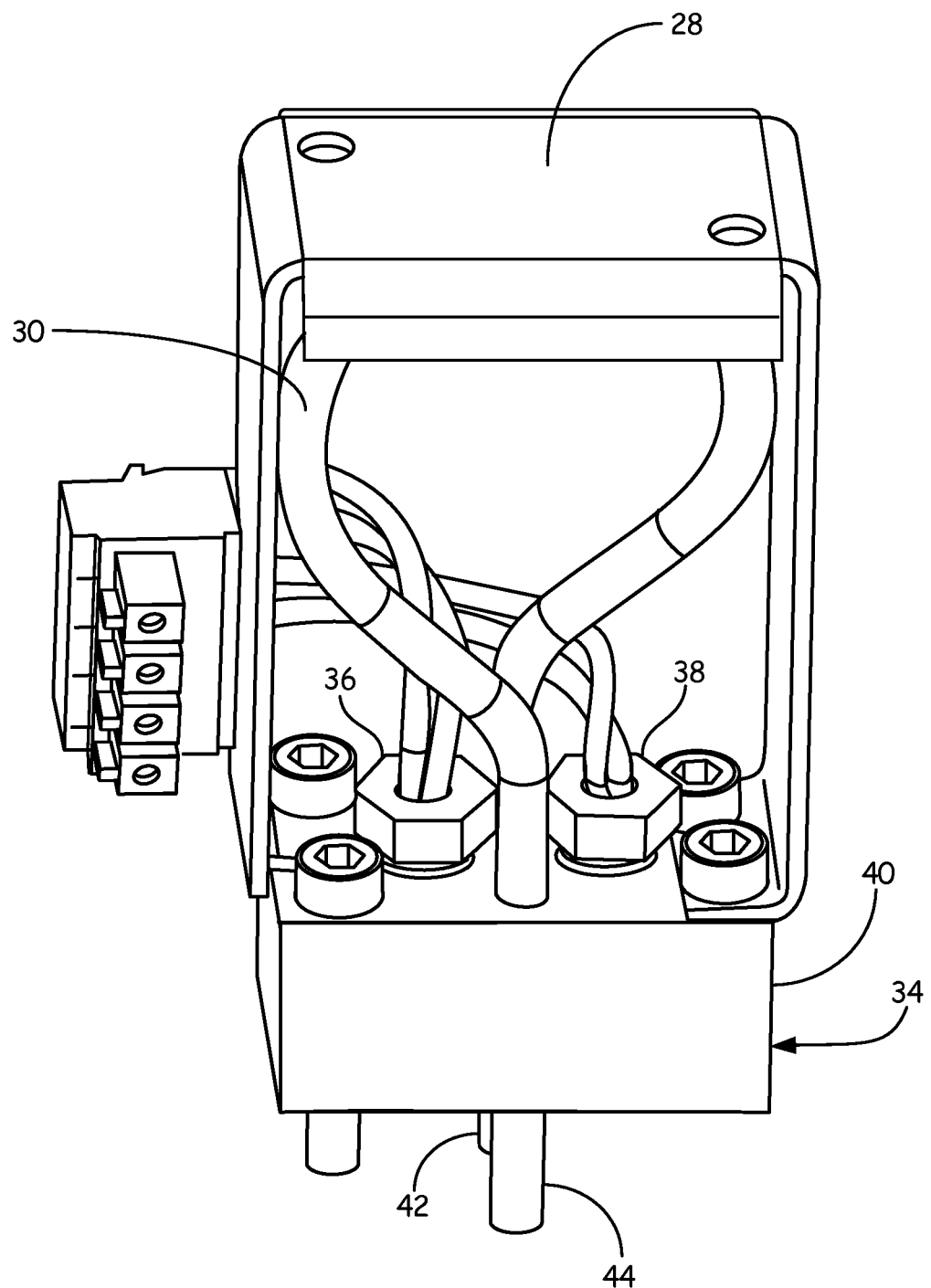
FIG. 2 is a diagrammatic perspective view of a thermal conductivity detector of a process gas chromatograph coupled to a heat pipe in accordance with an embodiment of the present invention.

FIG. 2 is a diagrammatic perspective view of a thermal conductivity detector of a process gas chromatograph coupled to a heat pipe. Thermal conductivity detector 34 includes a pair of thermal conductivity sensors 36, 38 mounted within metal block 40. Sensors 36, 38 sense thermal conductivity of a reference gas and a sample of interest flowing through block 40 in order to provide an indication of thermal conductivity relative to a reference gas and a sample of interest. Block 40 may be considered to be a thermal block in that the high thermal conductivity of the metal distributes heat quickly and effectively such that thermal conductivity sensors 36, 38 are maintained at the same temperature as one another. Sensors 36, 38 are coupled to measurement circuitry (not shown) in the process gas chromatograph such that the thermal conductivities can be processed to provide the analytic output. Heat pipe 30 includes two condensing ends 42, 44. Ends 42, 44 pass through block 40 and regions of heat pipe 30 near ends 42, 44 are in direct thermal contact with block 40. Additionally, as indicated in FIG. 2, the arrangement of sensors 36, 38 and the portions of heat pipe 30 passing through block 40 are preferably symmetrical such that heat flow is substantially identical for one sensor 36, 38 relative to the other sensor 38, 36.

Heat pipe 30 is preferably constructed from tubing formed of a metal with high thermal conductivity such as copper or aluminum. Additionally, given the precise nature of thermal control around 80° C., it is preferred that the working fluid of the heat pipe have a boiling point close to that value. One suitable example of a working fluid with a boiling point, at standard pressure, near 80° is ethanol. However, water can also be a suitable working fluid for an 80° C. control point if the pressure inside the heat pipe is reduced sufficiently. In at least some embodiments, it is also preferred that the entire assembly illustrated in FIGS. 1 and 2 be operated upside down such that the condensing ends 42, 44 of heat pipe 30 are above the evaporating loop coupled to shield 28. In this way, gravity will also assist with the return of condensate down from ends 42, 44 to the evaporative loop portion proximate shield 28.

Figure 3:
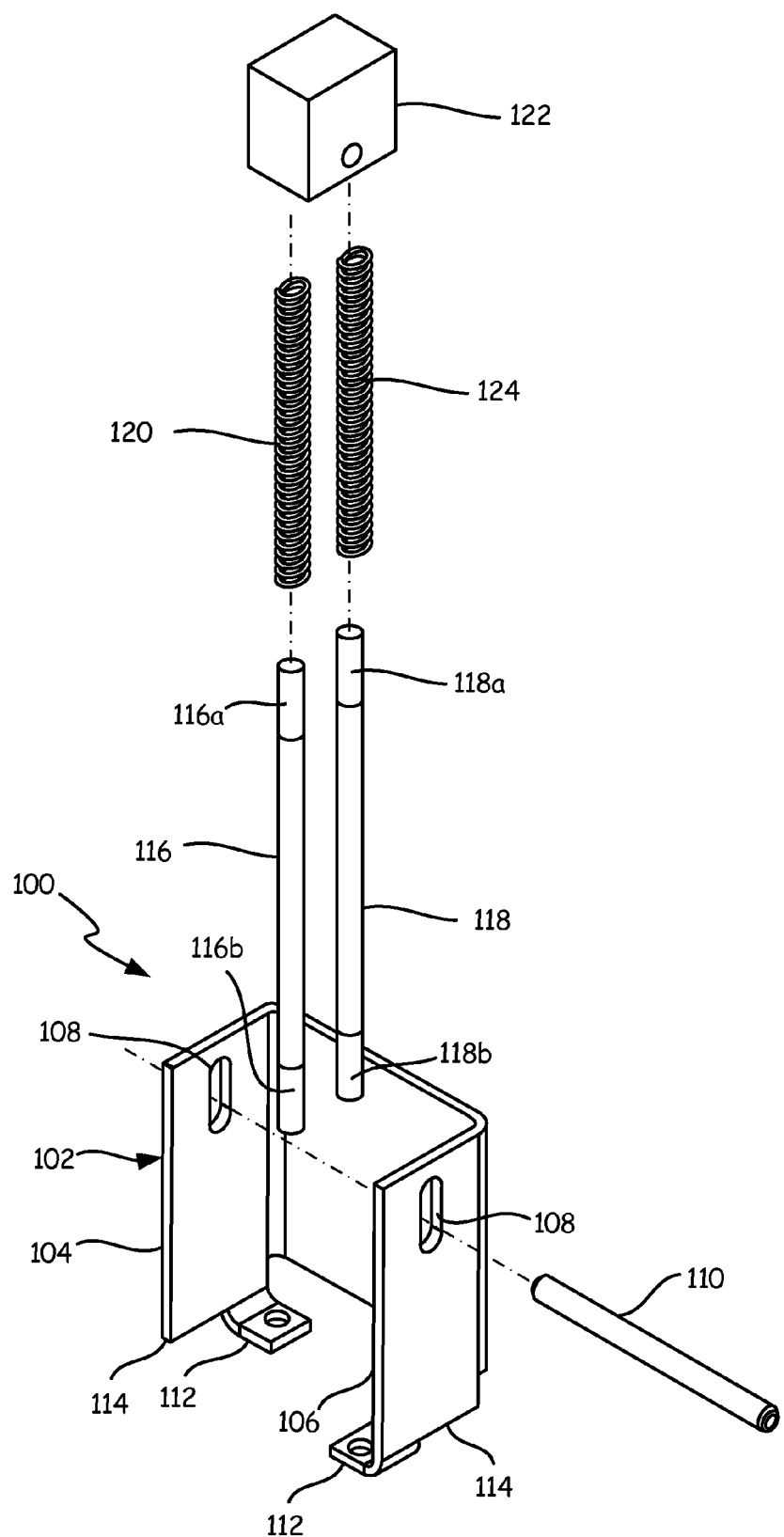
FIG. 3 is a diagrammatic exploded view of a heat pipe system employing a plurality of heat pipes in accordance with an embodiment of the present invention.

FIG. 3 is a diagrammatic exploded view of a heat pipe system employing a plurality of heat pipes in accordance with an embodiment of the present invention. The system shown in FIG. 3 is different than that shown in FIG. 2 in that a plurality of discrete heat pipes are used. System 100 includes frame 102, which has first and second opposing sides 104, 106. Each side 104, 106 can include a slot 108 that is sized to slidably receive retaining pin 110. In the embodiment shown in FIG. 3, each of sides 104, 106 also includes a mounting tab 112 extending inwardly from bottom end 114. Mounting tabs 112 have apertures therethrough allowing fasteners, such as those shown in FIG. 2, to mount frame 102 to metal block 40 (shown in FIG. 2). System 100 also includes a plurality of heat pipes 116, 118. In the embodiment shown in FIG. 3, each of heat pipes 116, 118 is substantially straight.

Heat pipe 116 has a first end 116a that is configured to slide through compression spring 120 into thermal block 122. Like block 40, thermal block 122 may be formed of metal and has a high thermal conductivity such that ends 116a and 118a are maintained at substantially the same temperature as one another. In one embodiment, heat transfer between first end 116a and thermal block 122 is increased by employing a thermal paste or heat transfer compound between end 116a and the inside diameter of a blind aperture within thermal block 122 that slidably receives first end 116a. One suitable example of such a thermal compound is sold under the trade designation AC-MX4 available from the Arctic Company of Switzerland. However, any suitable thermal paste or heat transfer compound with an operating temperature around 80° C. can be used. Heat pipe 116 also includes a second end 116b that is thermally coupled to a thermal conductivity sensor mounted within thermal block 40.

Heat pipe 118 has a first end 118a that is configured to slide through compression spring 124 into thermal block 122. In one embodiment, heat transfer between first end 116a and thermal block 122 is increased by employing a suitable thermal paste, such as that set forth above, between end 118a and the inside diameter of the aperture within thermal block 122 that receives first end 118a. Heat pipe 118 also includes a second end 118b that is thermally coupled to a thermal conductivity sensor mounted within thermal block 40.

In the embodiment illustrated in FIG. 3, heat pipes 116 and 118 are substantially parallel to one another and are mounted substantially vertically relative to metal block 40, which receives respective ends 116b and 118b. This arrangement is beneficial in that it allows thermal block 122 to slide axially while cover 20 is being screwed, pressed, clamped, or otherwise secured onto the gas chromatograph. Thus, as cover 20 is displaced axially, block 122 is urged downward and slides along heat pipes 116 and 118. However, compression springs 120 and 124 urge block 122 upwardly thereby ensuring sufficient thermal contact between block 122 and cover 20.

Figure 4:
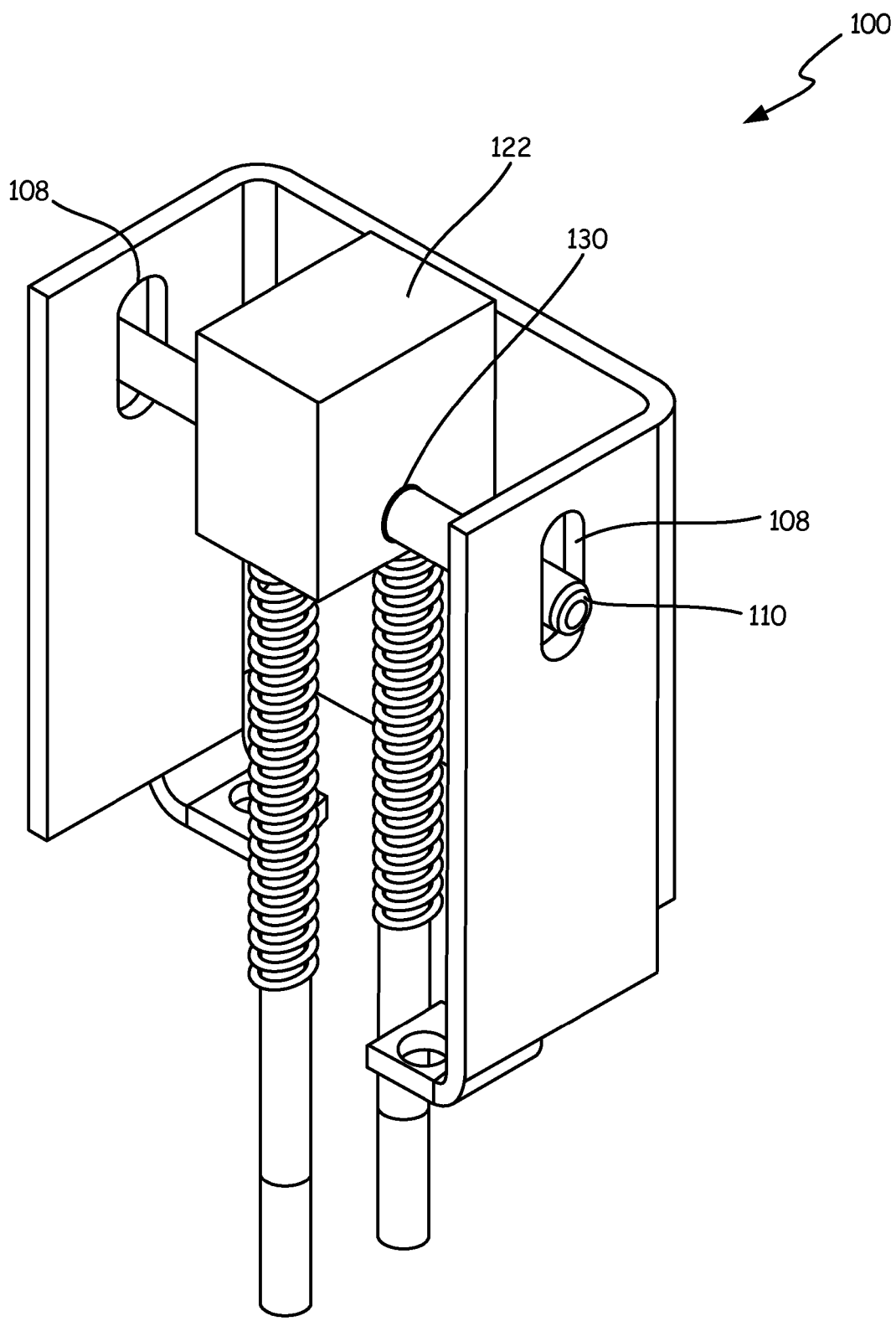
FIG. 4 is a perspective view of an assembled heat pipe system in accordance with an embodiment of the present invention.

FIG. 4 is a perspective view of an assembled heat pipe system in accordance with an embodiment of the present invention. In FIG. 4, retaining pin has passed through aperture 130 in block 122 and extends through each of slots 108. As block 122 moves up and down, its range of motion is limited by retaining pin 110 hitting top and bottom ends of slots 108. Additionally, if a given heat pipe needs replacement or repair, the entire assembly can be disassembled by simply removing retaining pin 110.

The embodiment described with respect to FIGS. 3 and 4 is believed to improve heat transfer from the metal cover wall to thermal detector(s) within the analytic device. The exterior of the enclosure is in contact with an electric heater and as the enclosure is heated, the interior is in turn heated via natural convection. It can be time consuming to get the thermal conductivity detectors within such analytic devices to be stabilized at the requisite operating temperature. It is believed that embodiments of the present invention will increase the efficiency of heat transfer and reduce the amount of time required for the thermal conductivity detector(s) to reach and stabilize at any given operating temperature.

While particular embodiments have been described, aspects of the present invention includes variations. For example, the heat transfer system may be designed with a single heat pipe. Further, additional heat pipes, beyond the two shown, can also be employed. Additionally, the type of springs or mechanical elements that urge block 122 into cover 20 can be varied. Suitable spring types include tension springs, constant force springs, bands, or any other suitable mechanical component. Additionally, various types of thermally conductive materials can be employed where desired. Finally, the heat pipes could be replaced with suitable thermally conductive rods or tubes.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A process analytic device comprising:
    an input to receive a sample of interest;
    an analytic detector operably coupled to receive the sample of interest and to provide an analytic output relative to the sample of interest; and
    a plurality of heat pipes thermally coupled to the analytical detector, wherein each of the plurality of heat pipes are substantially straiaht and parallel to one another; and
    wherein each of the heat pipes includes a first end thermally coupled to a thermal block and a second end thermally coupled to the analytic detector.

2. The process analytic device of claim 1, wherein the process analytic device is a process gas chromatograph.

3. The process analytic device of claim 1, wherein the thermal block is movable along the heat pipes as a cover of the process analytic device is secured.

4. The process analytic device of claim 3, and further comprising at least one compression spring disposed to urge the thermal block against the cover.

5. The process analytic device of claim 4, wherein one of the plurality of heat pipes is configured to slide through one of the at least one compression springs.

6. The process analytic device of claim 1, wherein the first end of each of the heat pipes is coupled to the thermal block using a heat transfer compound.

7. The process analytic device of claim 6, wherein the heat transfer compound comprises a thermal paste.

8. A heat pipe system for use in a process analytic device, the heat pipe system comprising:
    a first heat pipe;
    a second heat pipe;
    a first thermal block; and
    wherein each of the first and second heat pipes have a first end and a second end, wherein the first end of each of the heat pipes is configured to engage the first thermal block, and wherein the second end of each of the heat pipes engages a thermal conductivity sensor.

9. The heat pipe system of claim 8, wherein the thermal conductivity sensor is mounted within a second thermal block.

10. The heat pipe system of claim 8, wherein engaging the first thermal block comprises a connection between each of the heat pipes, and wherein the connection comprises a thermal paste positioned between each of the heat pipes and the first thermal block.

11. The heat pipe system of claim 8, wherein the first thermal block further comprises a plurality of apertures, and wherein engagement between the first end of each of the heat pipes and the first thermal block comprises the first end of each of the heat pipes being received within one of the plurality of apertures within the first thermal block.

12. The heat pipe system of claim 8, wherein the first end of each of the heat pipes is further configured to slide through a compression spring such that an end of the compression spring is in contact with the first thermal block.

13. The heat pipe system of claim 8, wherein the plurality of heat pipes are substantially parallel to each other.

14. The heat pipe system of claim 8, wherein the plurality of heat pipes are perpendicular to a side of the first thermal block.

15. A system for maintaining a substantially constant temperature of a component within an analytic device, the system comprising:
- a frame with a first side and a second side, wherein the first side opposes the second side;
- a thermal block positioned at a first end of the frame;
- the component being positioned at a second end of the frame; and
- a plurality of heat pipes, each being configured to engage the thermal block at a first end thereof and to engage the component at a second end thereof.

16. The system of claim 15, wherein each of the first and second sides further comprises a slot configured to receive a retaining pin such that the retaining pin extends at least from the first side to the second sides.

17. The system of claim 15, wherein the thermal block is urged away from the component.

\* \* \* \* \*